United States Patent
Cracowski et al.

(10) Patent No.: US 10,874,856 B2
(45) Date of Patent: Dec. 29, 2020

(54) DEVICE FOR TREATING A CUTANEOUS ULCER

(71) Applicants: CENTRE HOSPITALIER UNIVERSITAIRE GRENOBLE, La Tronche (FR); UNIVERSITE GRENOBLE ALPES, St. Martin d'Hères (FR)

(72) Inventors: Jean-Luc Cracowski, Saint Ismier (FR); Matthieu Roustit, Murianette (FR); Sophie Blaise, Villard Bonnot (FR)

(73) Assignees: Centre Hospitalier Universitaire Grenoble, Hopital Nord, La Tronche (FR); Universite Joseph Fourier—Grenoble 1, St. Martin d'Heres (FR)

( * ) Notice: Subject to any disclaimer, the term of this patent is extended or adjusted under 35 U.S.C. 154(b) by 436 days.

(21) Appl. No.: 14/904,796

(22) PCT Filed: Jul. 15, 2014

(86) PCT No.: PCT/EP2014/065093
§ 371 (c)(1),
(2) Date: Jan. 13, 2016

(87) PCT Pub. No.: WO2015/007712
PCT Pub. Date: Jan. 22, 2015

(65) Prior Publication Data
US 2016/0158543 A1    Jun. 9, 2016

(30) Foreign Application Priority Data
Jul. 15, 2013 (FR) ........................... 13 56941

(51) Int. Cl.
  A61N 1/30        (2006.01)
  A61N 1/32        (2006.01)
  (Continued)

(52) U.S. Cl.
  CPC ........ *A61N 1/325* (2013.01); *A61F 13/00063* (2013.01); *A61N 1/0428* (2013.01); *A61F 2013/00285* (2013.01)

(58) Field of Classification Search
  CPC ........ A61N 1/325; A61N 1/0436; A61N 1/30; A61N 1/0428; A61N 1/0432;
  (Continued)

(56) References Cited

U.S. PATENT DOCUMENTS 5,533,971 A * 7/1996 Phipps .................... A61N 1/30
                                                  604/20
7,945,320 B2 * 5/2011 Durand ................ A61K 9/0009
                                                  604/20

(Continued)

FOREIGN PATENT DOCUMENTS

WO   WO-2009/096822 A1   8/2009

OTHER PUBLICATIONS

Blaise, S., Roustit, M., Millet, C., Ribuot, C., Boutonnat, J. and Cracowski, J. (2011), Cathodal iontophoresis of treprostinil and iloprost induces a sustained increase in cutaneous flux in rats. British Journal of Pharmacology, 162: 557-565. doi:10.1111/j.1476-5381.2010.01045.x.*

(Continued)

*Primary Examiner* — Nathan R Price
*Assistant Examiner* — Courtney B Fredrickson
(74) *Attorney, Agent, or Firm* — Harness, Dickey & Pierce, PLC

(57) ABSTRACT

A device treats a region of the body of a patient having a cutaneous ulcer, including:

(Continued)

a hydrogel, hydrocolloid, hydrocellular or hydrofiber primary dressing, impregnated with treprostinil, that can be shaped to the contours of the region to be treated, a so-called "active" electrode in contact with the primary dressing, a so-called "passive" electrode at a distance from the active electrode, a DC generator, the terminals of which are connected to the electrodes, the cathode and the anode respectively forming the active electrode and the passive electrode for iontophoresis, so as to cause treprostinil to migrate by cathodal iontophoresis into the region to be treated.

21 Claims, 5 Drawing Sheets

(51) Int. Cl.
*A61N 1/04* (2006.01)
*A61F 13/00* (2006.01)

(58) Field of Classification Search
CPC .. A61N 1/0444; A61N 1/0484; A61N 1/0492; A61N 1/0496; A61N 1/303; A61K 9/0009
See application file for complete search history.

(56) References Cited

U.S. PATENT DOCUMENTS

| | | | | |
|---|---|---|---|---|
| 2003/0144625 | A1* | 7/2003 | Sherman | A61N 1/044 604/20 |
| 2004/0039328 | A1* | 2/2004 | Henley | A61N 1/30 604/20 |
| 2005/0038375 | A1* | 2/2005 | Nitzan | A61N 1/30 604/20 |
| 2005/0131338 | A1* | 6/2005 | Keusch | A61N 1/0448 604/22 |
| 2005/0165111 | A1* | 7/2005 | Wade | A61K 31/191 514/573 |
| 2011/0264028 | A1 | 10/2011 | Ramdas et al. | |
| 2014/0052051 | A1 | 2/2014 | Tagliaferri et al. | |

OTHER PUBLICATIONS

Blasie, S. et al., :"Cathodal Iontophoresis of Treprostinil Induces a Sustained Increase in Cutaneous Blood Flux in Healthy Volunteers," The Journal of Clinical Pharmacology, 2012, pp. 1-9.

Blaise, S. et al., "Cathodal iontophoresis of treprostinil and iloprost induces a sustaned increase in cutaneous flux in rats," British Journal of Pharmacology, 2011, pp. 557-565.

Trojanowska, M., "Cellular and molecular aspects of vascular dysfunction in systemic sclerosis," NIH Public Access, Aug. 2010, pp. 1-19.

Gabrielli, A. et al., "Scleroderma," The New England Journal of Medicine, May 7, 2009, pp. 1989-2003.

* cited by examiner

DEVICE FOR TREATING A CUTANEOUS ULCER

CROSS-REFERENCE TO RELATED APPLICATIONS

This application is a National Phase Entry of International Patent Application No. PCT/EP2014/065093, filed on Jul. 15, 2014, which claims priority to French Patent Application Serial No. 1356941, filed on Jul. 15, 2013, both of which are incorporated by reference herein.

FIELD

The present invention relates to a device for treating cutaneous ulcer, in particular in systemic scleroderma.

BACKGROUND

Systemic scleroderma is a rare, particularly disabling disease (affecting about 50 to 300 patients per million inhabitants) that mostly affects women (about 3 to 14 women per man). This disease is characterized by cutaneous and visceral fibrosis associated with diffuse microvascular damage and the presence of autoantibodies directed against cellular antigens. For a detailed general description of this disease, reference can be made to the review by Gabrielli et al. [1].

Scleroderma is divided into two principal categories:
  limited cutaneous scleroderma, wherein fibrosis is limited essentially to the hands, arms and face.
  diffuse cutaneous scleroderma, a rapidly progressing disease that affects most of the skin and internal organs.
There are also forms without skin damage and border forms with other connectivities.

Vascular dysfunction is a key component in the pathogenesis of this disease, preceding fibrosis. In this respect, reference can be made to the detailed general review by Trojanowska [2]. This dysfunction chiefly concerns microcirculation, but conducting arteries are also affected. The microcirculation has structural and functional abnormalities, which are interdependent. This microangiopathy is characterized on a structural level by capillary rarefaction, development of megacapillaries, and vascular obstruction.

On a functional level, the first sign of microvascular dysfunction is a Raynaud's phenomenon, which can be associated with cutaneous trophic disorders and pulmonary hypertension. Raynaud's phenomenon, which can be primary or secondary, is the clinical syndrome corresponding to exaggerated vasoconstriction of the microvessels of the fingers and/or toes and/or ears in response to environmental stress (cold, more rarely dampness) or emotional stress. Raynaud's phenomenon in scleroderma is distinguished from primary Raynaud's phenomenon by crises of greater severity and frequency more often affecting regions other than the hands, such as the nose, tongue, ears, toes. Few therapeutic classes are effective in treating Raynaud's phenomenon in scleroderma.

Digital ulcers are the most severe and most disabling complication of systemic scleroderma. Their frequency is estimated at 43% in the limited cutaneous forms and at 51% in the diffuse cutaneous forms. The physiopathology involves vascular ischemia and mechanical factors associated with sclerotic skin under tension. The treatment of digital ulcers in systemic scleroderma is first and foremost preventive, in the context of good cutaneous and ungual hygiene.

In terms of a cure, intravenous iloprost is the only drug recommended in a five-day treatment for severe Raynaud's phenomenon. This drug has shown its superiority over conventional therapies for severe digital ischemia and digital gangrene. In a randomized study against placebo, iloprost provided an advantage in terms of the frequency of Raynaud's attacks and the healing time of ulcers.

Used in an open study in the form of one perfusion per week every six weeks over a period of 12 months, intravenous iloprost provides an advantage against Raynaud's phenomenon and could have an effect on the progression of the disease, as attested by the improvement in skin scores; on the other hand, the effect on sclerodactyly remains much debated. Bosentan, a nonreceptor antagonist of endothelin receptors ETA and ETB, showed in the context of the RAPIDS-2 study that it significantly reduced the risk developing new ulcers. However, bosentan showed no advantage in healing preexisting ulcers and has, consequently, a marketing authorization in Europe only for preventing digital ulcers in systemic scleroderma patients with recurrent active digital ulcers. It should be noted that bosentan does not improve Raynaud's phenomenon. Studies with sildenafil in digital ulcers are currently underway. Digital sympathectomy is proposed by certain authors in the most severe cases.

In summary, Raynaud's phenomenon in scleroderma is a source of severe functional difficulty while digital ulcers in scleroderma are a frequent and extremely disabling phenomenon that can progress so far as to necessitate the amputation of one or more fingers and represent the first source of functional handicap in these patients. Treatment of peripheral vascular symptoms in 2012 is limited and only partially effective (only three grade—A recommendations by the European League Against Rheumatism (EULAR)): calcium inhibitors in the treatment of Raynaud's phenomenon, oral endothelin antagonists (bosentan) indicated in the prevention of digital ulcers, intravenous prostacyclin analogues (iloprost) as a cure at the cost of very frequent adverse effects (headache, vasomotor flushing, nausea, vomiting, maxillary pain, myalgia).

Pharmacologically, the difficulty in treating Raynaud's phenomenon and digital ulcers in scleroderma is that the diffusion into the tissue of the rare systemic drugs that target microangiopathy is limited by capillary rarefaction in the affected tissues. This limited diffusion is difficult to compensate for by increasing the doses to be administered, given the frequent systemic adverse effects of iloprost. Work carried out on rats and then on healthy volunteers showed the effect of treprostinil (Remodulin®), a prostacyclin analogue, applied by cathodal iontophoresis, on increasing skin blood flow.

Iontophoresis consists in applying to the skin low-strength current (generally 20 to 100 µA) through a capsule or a sponge containing ionized drug, in order to cause a transcutaneous migration of this drug. Depending on the characteristics of the molecule, the target tissue and the concentrations used, the pharmacodynamic effect could be limited to the dermis, while in other cases the molecule diffuses into the body with or without systemic action as a function of the concentrations reached. This drug delivery method is noninvasive and has several advantages over conventional passive transdermal administration: faster release of the drug into the skin, better control of the amount administered, ability to diffuse charged molecules or macromolecules into the skin.

FIG. 1 is a schematic illustration of the principle of iontophoretic transport. The iontophoresis device comprises two electrodes: an anode A and a cathode C applied to a patient's skin and connected to an electric generator G.

Two mechanisms are involved in iontophoretic transport. First, electromigration is the movement of ions through a membrane (here the skin) under the direct influence of an electric field. Negatively charged drugs will be pushed into the skin under the cathode, while the transfer of positively charged drugs occurs at the anode. The second mechanism is called electroosmosis, which can be diagrammed as the volumetric flow rate produced by the passage of current.

Since the isoelectric point (pi) of human skin is about 4 to 4.5, which is lower than physiological pH, skin is negatively charged. The application of an electric field through the skin promotes cation circulation. Consequently, the volumetric flow rate is directed in the direction anode-cathode, which facilitates the transport of positively charged drugs. Electroosmosis also enables the diffusion of neutral molecules by anodal iontophoresis. The respective electromigration or electroosmosis portion of the transfer strongly depends on the physicochemical properties of the molecules and the polarity of the current applied.

As illustrated in FIG. 1, positively charged drugs ($D^+$) migrate under the anode while negatively charged drugs ($D^-$) migrate under the cathode. The epidermis is labeled ed, the dermis d, and the hypodermis hd. Arrows F1 and F2 represent anodal and cathodal electromigration, respectively, while arrow F3 represents electroosmosis.

The Inventors first tested in animals several candidate molecules with different current polarities (anodal and cathodal), these molecules being contained in a liquid solution in direct contact with the animal's skin, and showed that in rat treprostinil caused cutaneous vasodilatation after 20 minutes of cathodal iontophoresis at 100 µA [3]. These preclinical data suggest a concentration-dependent effect persisting at least 60 minutes after iontophoresis is over. This effect is specific to cathodal iontophoresis, with no effect on skin blood flow being observed absent current or with anodal current. No sign of local toxicity was observed, clinically and after systematic skin biopsies.

A clinical study then included 20 healthy volunteers. These subjects received 3 concentrations of treprostinil via continuous cathodal iontophoresis on the forearm for 20 minutes and a control iontophoresis of 0.9% NaCl. Skin blood flow was quantified by laser Doppler imaging. Treprostinil at 250 µM causes an increase in cutaneous vascular conductance ($AUC_{80\ min}$ (31,897±24,390% BL·min) compared to the 0.9% NaCl control (p<0.005), 2.5 µM treprostinil (p<0.005) and 25 µM treprostinil (p<0.005) [4]. This was confirmed when the flow was recorded for a maximum of 10 hours.

FIG. 2 illustrates the effect on the forearm of the iontophoresis (20 minutes, 20 µA, represented by the solid rectangle) of 250 µM treprostinil (curve (a)), 25 µM treprostinil (curve (b)) and 2.5 µM treprostinil (curve (c)), versus 0.9% NaCl (curve (d)) as a function of time t. Curve (e) shows the effect of 250 µM treprostinil applied without iontophoresis. This effect is expressed as cutaneous vascular conductance (CVC; percentage of the baseline) recorded up to 24 hours.

To implement iontophoresis on the forearm, several iontophoresis chambers containing treprostinil liquid solution in contact with a cathode, and an anode at a distance of about 15 cm from the cathode, are placed on the inside of the forearm of each patient. Each iontophoresis chamber had a circular surface area of 1.2 $cm^2$ and contained 360 µl of treprostinil solution. Treprostinil liquid solution was in direct contact with the subject's skin.

Treprostinil was tested at concentrations of 2.5 µM, 25 µM and 250 µM; NaCl solution was also used for comparison. However, the tests carried out to date have been on healthy subjects, and consequently on undamaged skin, and further on a region of the body that is not representative of the site of sclerodermic ulcers. In particular, the inside of the forearm is broad and flat, which facilitates the attaching of the iontophoresis chamber and the placement of the anode at sufficient distance from the cathode. Moreover, the subject was immobilized during the tests.

It would now be desirable to have at one's disposal a device for treating scleroderma patients. However, even if they appear promising, the results of the studies described above are not directly transposable to the treatment of ulcers. For example, ulcers are not found in regions as flat as the inside of the forearm.

In particular, digital ulcers are found on the finger pad, which is a non-flat surface of limited area. Moreover, the surface area covered by each iontophoresis chamber used experimentally is too small relative to the surface area to be covered for a clinical application. In addition, the device must also perform a function of protecting ulcers from the external environment.

The following problems thus arise:
first, attaching the iontophoresis device on the region to be treated for a long period, without hindering patient activity,
covering a surface area corresponding to the surface area of the ulcer or the surface area of the region where the appearance of such an ulcer is sought to be prevented,
locating the anode at a distance from the cathode sufficient to allow iontophoretic transport, while providing the least bulky device possible,
finally, as this device is intended to be discarded after use, producing said device at a reasonable cost.

At present, there is no iontophoresis device adapted to treat skin lesions over long periods. A known iontophoresis device, such as the Lidosite® device from the company Viterys, is intended for local anesthesia by iontophoresis of lidocaine. However, this device must be applied to undamaged skin; in addition, at the conclusion of the treatment, which is very short (about 10 minutes), the device must be removed.

Another device, named Ionsys™, is under development by the company Incline Therapeutics for purposes of analgesia. However, like the previous, this device is intended to be applied on healthy skin. An aim of the invention is thus to design a device for treating skin lesions, in particular ulcers, in a scleroderma patient.

SUMMARY

In accordance with the invention, a device is proposed for treating a region of the body of a patient having a cutaneous ulcer, comprising:
a hydrogel, hydrocolloid, hydrocellular or hydrofiber primary dressing, impregnated with treprostinil, that can be shaped to the contours of the region to be treated,
a so-called "active" electrode, in contact with said primary dressing,
a so-called "passive" electrode, at a distance from the active electrode,
a DC generator, the terminals of which are connected to said electrodes, the cathode and the anode respectively forming the active electrode and the passive electrode for iontophoresis, so as to cause treprostinil to migrate by means of cathodal iontophoresis into the region to be treated.

It is recalled that a primary dressing is a dressing specially adapted for application on a wound, the function of such a dressing being to create a damp microclimate around the wound to promote healing while forming a bacteriological barrier. Such a dressing is thus permeable to gas exchange, impermeable to liquids, able to drain exudates, and sterile, without sticking to the wound. The choice of dressing type from among hydrogel, hydrocolloid, hydrocellular or hydrofiber dressings is made by the skilled person depending on the nature of the wound to be treated.

In a particularly advantageous manner, the concentration of treprostinil impregnating the primary dressing is between 0.25 mM and 25 mM. According to an embodiment, the active electrode consists of conductive ink deposited on the primary dressing. Preferably, the DC generator is designed to generate direct current having a strength between 20 $\mu A/cm^2$ and 100 $\mu A/cm^2$. In a particularly advantageous manner, said DC generator is borne by a support adapted to be attached to the patient's skin.

According to an embodiment of the invention, said DC generator is integral with the primary dressing and the active and passive electrodes. According to a particular embodiment, the device comprises a secondary dressing that can be shaped to the contours of the region to be treated, said secondary dressing supporting the primary dressing in contact with the active electrode, the passive electrode and the DC generator. According to an embodiment, the device comprises a module comprising the passive electrode and the DC generator, said module being distinct from the primary dressing and adapted to be connected to the active electrode. Advantageously, the surface area of the primary dressing is between 5 $cm^2$ and 100 $cm^2$.

According to a preferred embodiment of the invention, the device is provided in a form adapted to be slipped onto the patient's finger, the primary dressing and the active electrode being adapted to be shaped to the pad of said finger and the passive electrode being adapted to be shaped to the outer face of the finger opposite the pad. The device can further comprise a secondary dressing that can be shaped to the contours of the region to be treated, intended to cover the primary dressing.

BRIEF DESCRIPTION OF THE DRAWINGS

Other features and advantages of the invention will become apparent from the following detailed description in reference to the accompanying drawings wherein.

DETAILED DESCRIPTION

Figure 1:
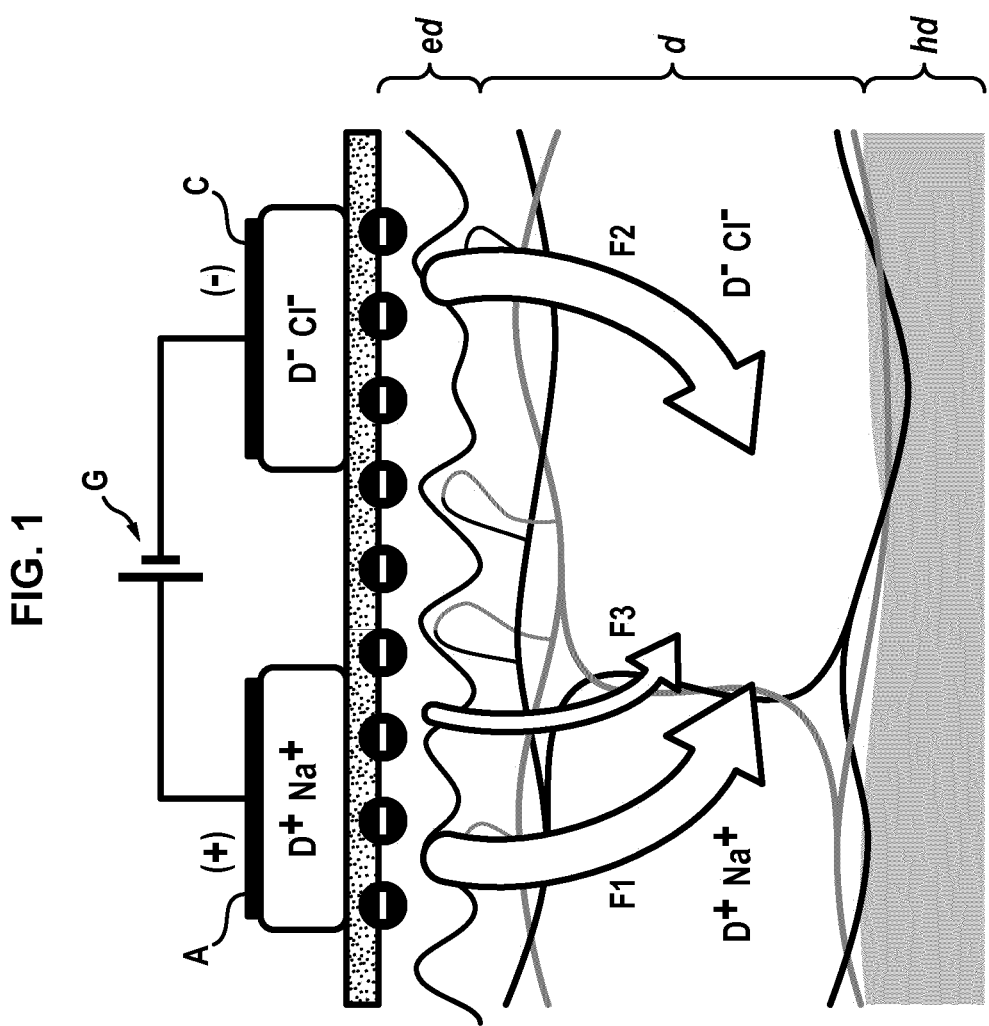
FIG. 1 is a diagram of the principle of iontophoretic transport.
Figure 2:
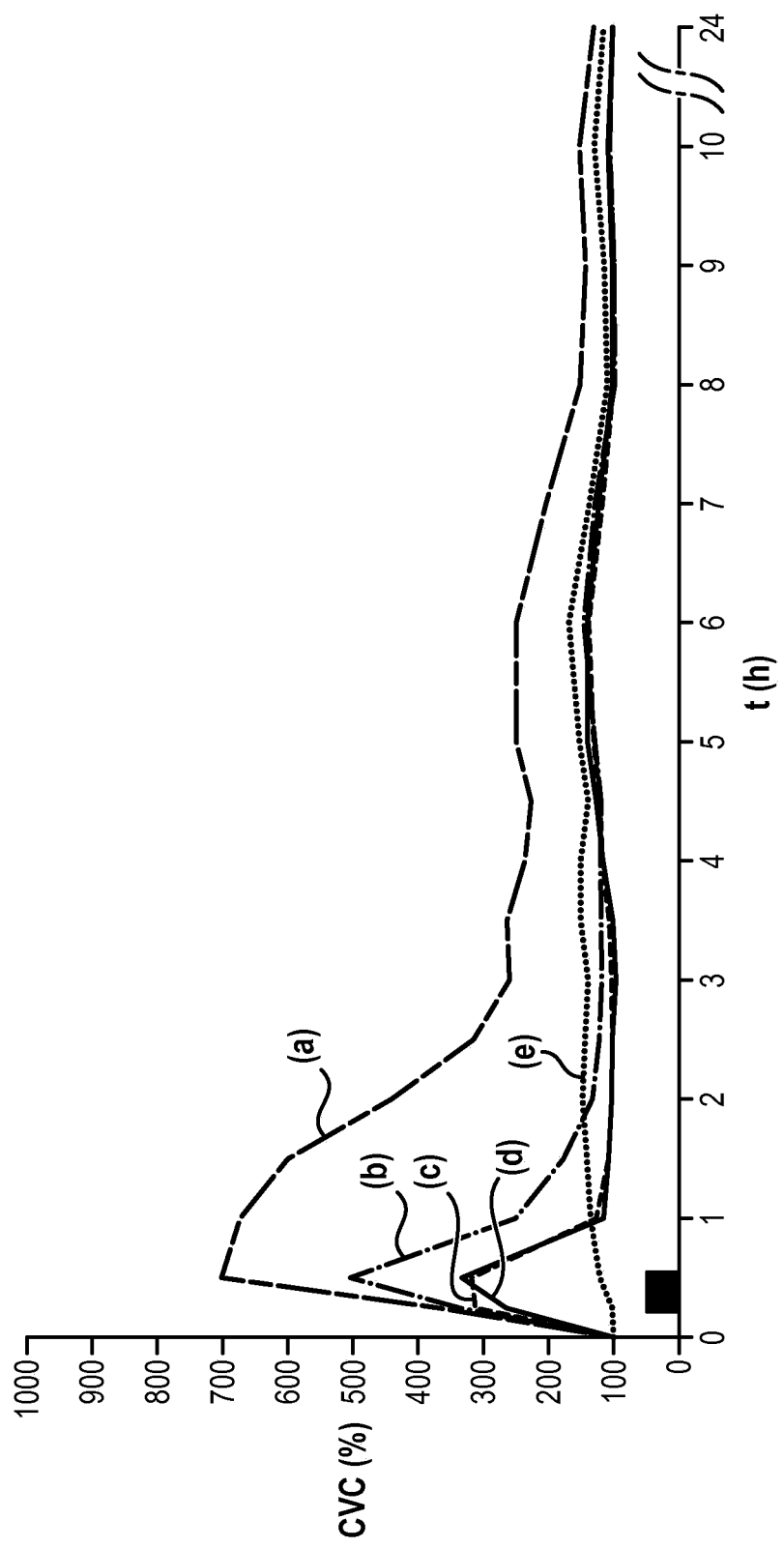
FIG. 2 shows the effect on cutaneous vascular conductance of the forearm of a healthy subject of various concentrations of treprostinil in liquid solution form applied by iontophoresis.

The Inventors showed the efficacy in terms of vasodilatation of an iontophoresis treatment by means of a primary dressing impregnated with treprostinil. They also showed that treprostinil was present (quantification by high-performance liquid chromatography coupled to tandem mass spectrometry in dermal dialysate fluid collected by microdialysis fibers) in the dermis of the forearm for an average of up to 8 hours. The use of treprostinil to impregnate a primary dressing has the advantage of making it possible to cover larger areas of skin. However, it was not obvious that the results obtained by iontophoresis of treprostinil in liquid solution form in direct contact with the patient's skin could be obtained with the embodiment in accordance with the invention.

First, the fact that iontophoresis causes vasodilatation with a liquid solution does not suggest the same effect when the drug is impregnated into a primary dressing. Furthermore, it could be a concern that impregnating the dressing would prevent—or at least strongly hinder—the migration of molecules toward the region to be treated, all the more so since the skin of scleroderma patients is substantially thicker than that of healthy subjects. In addition, the efficacy of treprostinil in liquid solution form was shown under specific conditions of concentration and applied current, which are not applicable to an impregnated dressing.

Indeed, the applied electric field being different, the molecular diffusion generated by this electric field is necessarily different. An efficacy inferior to that of iontophoresis of treprostinil in liquid solution form was thus expected. Furthermore, the application of electric current is likely to cause discomfort, even lesions, in the patient if the current density (strength per unit area) of said current is too high.

Among the risks associated with iontophoresis, mention may be made of paresthesia, itching, burning sensations, erythema and even burns. However, the Inventors succeeded in defining the conditions for implementing iontophoresis that make it possible, even with a primary dressing impregnated with treprostinil, to obtain in the patient the effects observed in the preliminary experiments, without causing notable adverse effects in the patients.

Another obstacle overcome by the Inventors is obtaining a pharmacological effect of the dressing on sclerotic skin, whereas the iontophoresis devices to date have always been applied to healthy skin. As a result, existing iontophoresis devices employ supports, for example in the form of sponges, which are unsuited—in terms of safety—for placement in contact with wounds. This application required the development of a primary dressing specifically adapted to contact with damaged skin.

Lastly, the device in accordance with the invention is intended to be worn by the patient for a long period of time (typically at least a few hours). However, the fact that the patient's skin is in extended contact with an active substance is likely to involve the systemic passage of treprostinil. The Inventors thus assayed treprostinil in the plasma using high-performance liquid chromatography coupled to tandem mass spectrometry after iontophoresis for 20 minutes on the forearm and for 2 hours on the fingers. Systemic quantification made it possible to demonstrate negligible systemic passage.

Figure 3:
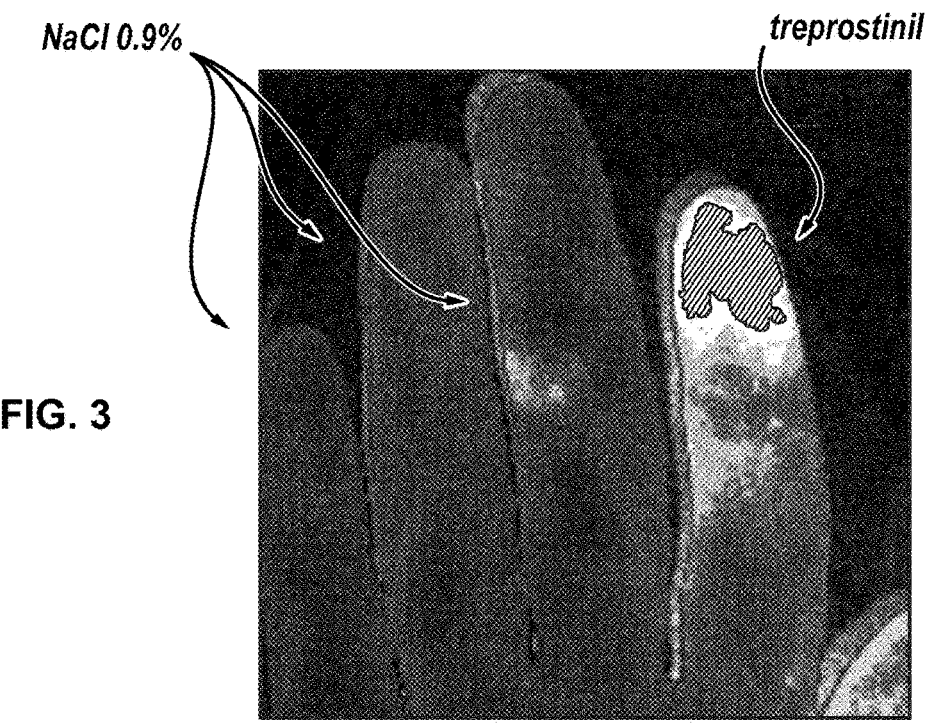
FIG. 3 is an image obtained by laser speckle contrast imaging of blood flow in the pad of the index finger treated by iontophoresis of treprostinil impregnating a primary dressing and in the pad of the middle finger of the same hand treated by NaCl iontophoresis, in a healthy subject.
Figure 4:
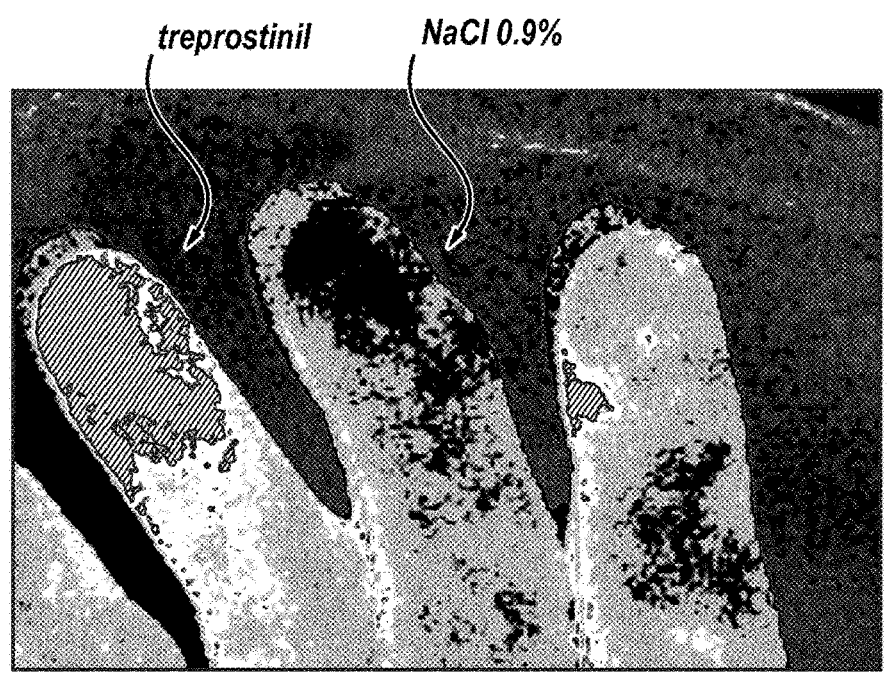
FIG. 4 is an image obtained by laser speckle contrast imaging of blood flow in the pad of a ring finger treated by iontophoresis of treprostinil impregnating a primary dressing and in the pad of the middle finger of the same hand treated by NaCl iontophoresis, in a subject with scleroderma.
Figure 5:
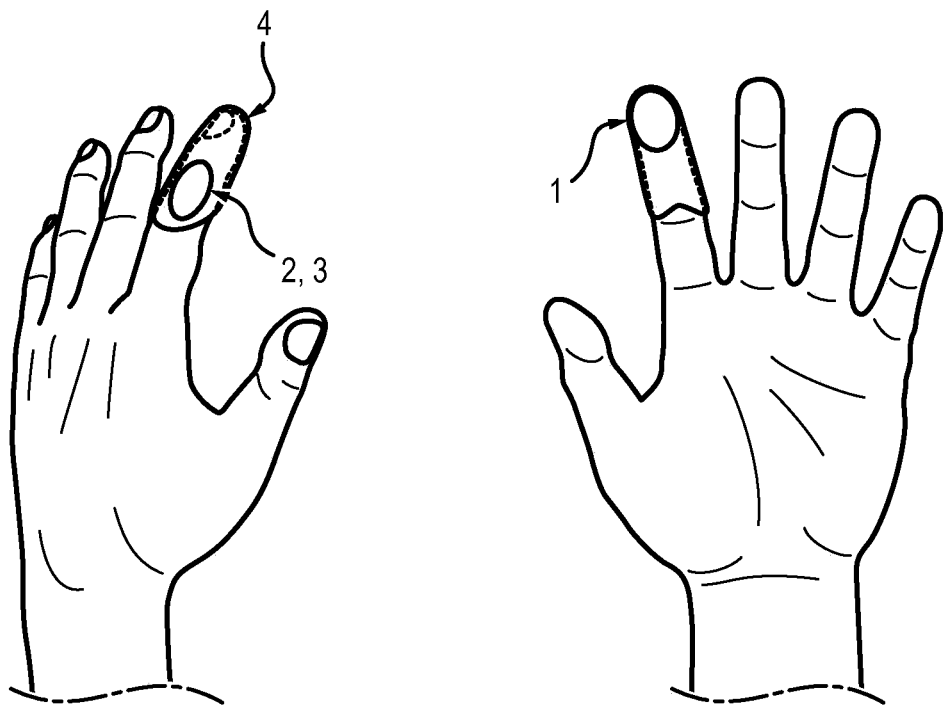
FIG. 5 is a diagram of a device according to an embodiment of the invention intended to be applied to the finger pad, wherein the electrodes and the generator are integrated into the primary dressing.

FIGS. 3 and 4 show the vasomotor effect of treprostinil impregnating a primary dressing applied to the finger pad, respectively in a healthy subject and a subject with scleroderma. FIG. 3 reproduces an image obtained by laser speckle contrast imaging of blood flow in the pad of the index finger treated by iontophoresis of treprostinil impregnating a primary dressing and in the pad of the middle finger of the same hand treated by iontophoresis of 0.9% NaCl impregnating another primary dressing, in a healthy subject. The iontophoresis was carried out under the following conditions: 240 mC/cm$^2$, direct current. Two 7.2 cm$^2$ Ag—AgCl electrodes (Iogel, Iomed Inc., Salt Lake City, Utah, USA) were soaked in 1.5 ml of treprostinil or NaCl solution (double-blind).

These drug-soaked electrodes were connected to the cathode, while the anode was connected to passive electrodes attached at a distance of 10 cm. Low-voltage computer-controlled generators were used (PF 751 Perilont USB Power Supply, Perimed, Järfålla, Sweden). The voltage was recorded continuously in order to estimate the skin's resistance.

On the middle finger, no effect of iontophoresis is observed. On the index finger, the various regions, represented on the original images by a color scale, show the various blood flows of the pad treated with treprostinil. The hatched region $I_1$ corresponds to high blood flow, the white region $I_2$ corresponds to moderate blood flow, and the dark region $I_3$ corresponds to low blood flow.

FIG. 4 reproduces an image obtained by laser speckle contrast imaging of blood flow in the pad of a ring finger treated by iontophoresis of treprostinil impregnating a primary dressing and in the pad of the middle finger of the same hand treated by iontophoresis of 0.9% NaCl, in a subject with scleroderma. The variation in blood flow is represented in same manner as in FIG. 3. This is thus the first demonstration of transcutaneous passage of treprostinil through damaged, i.e., sclerotic, skin. As in FIG. 3, a marked vasomotor effect is observed on the pad of the finger treated by treprostinil iontophoresis (ring finger) and no effect is observed on the pad of the finger treated with the reference NaCl solution (middle finger).

A study was conducted on 12 scleroderma patients and showed that cathodal iontophoresis of 250 μM treprostinil, in direct current, at 240 mC/cm$^2$, is well tolerated and associated with an increase in skin blood flow. Plasma samples taken from each patient 30 minutes post-iontophoresis had a treprostinil concentration below 1.8 pg/ml. Generally, the treatment device comprises a primary dressing impregnated with treprostinil. The primary dressing is intended to be applied directly to the patient's damaged (ulcerated) skin, and is thus made of material suited to this application.

Advantageously, the primary dressing is selected from one of the following four types of dressings:
 a hydrogel dressing,
 a hydrocolloid dressing,
 a hydrocellular dressing,
 a hydrofiber dressing.

These various types of dressing currently exist on the market and the skilled person is capable of selecting, from the available dressings, the one most suited to the intended application. The composition of these various dressings will thus not be described in detail herein, it being well documented in the scientific literature.

A hydrogel dressing is well suited to dry, fibrinous or necrotic wounds, while a hydrocolloid, hydrocellular or hydrofiber dressing is preferred in the granulation phase. In all cases, the primary dressing is sufficiently flexible to allow it to be shaped to the contours of the region to be treated, i.e., to follow the contour of said region in order to be in contact with substantially the entire surface of the region to be treated. In addition, the flexibility of the primary dressing prevents the exertion of excessive pressure on the skin, which would increase the risk of skin damage.

Depending on the case, the primary dressing can be provided in flat form and be shaped by the user to the region to be treated when placed on said region. Alternately, the treatment device can be provided to the user with the primary dressing shaped beforehand to the region to be treated. For example, if the device is intended to treat a finger pad, the device is provided as a finger stall the dressing of which occupies at least the portion intended to be in contact with the pad.

The surface area of the primary dressing depends on the region to be treated. The surface area of the primary dressing is selected according to the surface area of the wounds to be treated, while limiting the risk of systemic exposure to treprostinil. Typically, the primary dressing has a surface area between 5 cm$^2$ and 100 cm$^2$.

Whatever type of primary dressing is selected, it is impregnated with treprostinil liquid solution. Treprostinil is a synthetic analogue of prostacyclin, currently marketed under the name Remodulin®. The volume of treprostinil depends on the nature, the surface area and the thickness of the primary dressing.

The objective is for the volume of treprostinil solution to saturate the dressing so as to enable the molecule to come into contact with the skin. To this end, either real-time impregnation (the solution being deposited on the dressing just before application) or integrated pre-impregnation (dressing "crimped" with treprostinil) can be envisaged, in the latter case subject to confirmation of the product's stability. The treprostinil concentration is selected from the concentrations whose efficacy in impregnated form has been shown by the Inventors. Thus, the treprostinil concentration is preferably between 0.25 mM and 25 mM.

The treatment device further comprises an active electrode in contact with the primary dressing, from the side opposite that intended to be in contact with the patient's skin. This active electrode is designed to be connected to a terminal of an electric generator. As indicated below, the electric generator can be an integral part of the treatment device, but it can also be distinct therefrom.

In any case, the active electrode comprises a connector enabling it to be connected to a terminal of such an electric generator. As regards cathodal iontophoresis, the active electrode is intended to constitute the cathode of the device. Preferably, the electrode is made of material that helps minimize the size of the device without diminishing the ability of the dressing to be shaped to the contours of the region to be treated. The thickness of the active electrode is advantageously less than or equal to 500 μM.

According to an advantageous embodiment, the active electrode consists of conductive ink (for example of silver) deposited on the primary dressing. The surface area of the active electrode must be sufficiently large on the one hand to cover the surface of the treprostinil-soaked dressing and on the other hand to allow a low-density electric charge that does not cause a local reaction. The treatment device further comprises a passive electrode, which is arranged at a distance from the active electrode.

Preferably, the distance between the active electrode and the passive electrode is made as large as possible. The passive electrode is intended to constitute the anode of the iontophoresis device. It is thus designed to be connected to the other terminal of the DC generator mentioned above.

According to an embodiment, the passive electrode is an integral part of the device, i.e., it is provided to the user integral with the primary dressing and the active electrode, which facilitates the placing of the device on the patient. Alternately, the passive electrode is provided separately from the primary dressing and the active electrode. In this case, the user successively applies the primary dressing and the passive electrode and then connects same to the DC generator.

To minimize the bulk of the treatment device, the passive electrode is preferably made of a material that is sufficiently thin and flexible to be able to follow the contours of the region to which it is applied. The passive electrode, for example, is formed on an adhesive support enabling it to be attached to the patient's skin. The passive electrode consists of flexible metal and adhesive, and must be able to be shaped to the intended use.

The surface area of the passive electrode is, if possible, equivalent to that of the active electrode so that the charge density remains modest and does not cause paresthesia when the generator is turned on. To diffuse treprostinil into the region to be treated, direct current having a strength typically between 20 $\mu A/cm^2$ and 100 $\mu A/cm^2$ is applied by means of a suitable generator. According to an embodiment, the DC generator is distinct from the treatment device: it can be a commercially-available generator to which a user connects each of the active and passive electrodes. In this case, the size of the generator matters little.

Given the constraint represented by having the user connected to a stationary generator, the iontophoresis treatment can be applied discontinuously, i.e., electric current is applied only during limited time ranges and then the generator is disconnected to allow the patient to attend to her daily affairs. This method is enabled by the fact that the effect of treprostinil continues for a certain period after the end of the iontophoresis, as shown in FIG. 2 and also as shown by the persistence in the dermis of treprostinil up to 8 hours post-iontophoresis. To maximize the treatment's efficacy, it is made so that the time ranges over which the direct electric current is applied are sufficiently close together to avoid too great a decrease in the effect of treprostinil.

According to another embodiment, the DC generator is part of the treatment device, i.e., it is adapted to be worn by the patient. This allows, on the one hand, the patient to freely attend to her daily affairs and, on the other hand, the treatment to be applied without interruption in order to take advantage of the maximum effect of treprostinil. In this case, given the constraints related to the device's bulk and comfortable use, a miniaturized electric current generator is used.

For reasons of safety, the generator comprises an automatic shut-off system when over-voltage is detected. The generator can preferably be powered by a cell or a battery. Advantageously, the generator can further comprise a load indicator and an electrical circuit integrity indicator. These functionalities are known in themselves and thus will not be described in detail in the present text.

The electric current generator can be provided on the same support as the primary dressing and the active and passive electrodes, which makes it possible to connect the components during the manufacture of the device and to provide the user with a ready-to-use device requiring no assembly or connection. Maximum ease of use of the device is thus achieved. According to another embodiment, the miniature DC generator is borne by a support adapted to be attached to the patient's skin, and which also supports, preferably, the passive electrode.

Thus, the user receives the treatment device in two parts (the first comprising the primary dressing and the active electrode, the second being a module comprising the generator and the passive electrode), and it suffices to connect the generator to the active electrode to enable its operation. This makes it possible, if need be, to place the active electrode and the passive electrode at a great distance from each other, without the need for them to be borne by the same support, which would thus be bulky. All the parts of the device intended to be in contact with the patient's skin, and in particular the primary dressing, are sterile. After the device is manufactured, it is thus packaged in such a way as to maintain this sterility. Furthermore, the device is disposable, i.e., it is thrown away after use in iontophoresis treatment and/or when an insufficient amount of treprostinil remains in the primary dressing. Lastly, given the possibility of storing the device before use, the components, and in particular the treprostinil, are selected to have a sufficiently long shelf life, for example of at least one year.

According to an embodiment of the invention, the primary dressing is itself designed not only to serve as the support for treprostinil and the active electrode, but also to protect the treated region from the external environment. The primary dressing thus also performs the function of secondary dressing, which can be provided, for example, by an outer layer that is impermeable to bacteria, limits stains and perhaps absorbs impacts. Such can be the case of a hydrocolloid, hydrocellular or hydrofiber dressing.

Alternately, the treatment device can comprise a secondary dressing distinct from the primary dressing, intended to cover said primary dressing once placed on the region to be treated. Such is the case in particular when the primary dressing is a hydrogel. This secondary dressing must make it possible to limit contamination and to absorb impacts. In the case where the region to be treated has a pronounced curvature, the secondary dressing can further help keep the primary dressing in contact with the skin so as to allow an optimal diffusion of treprostinil.

FIG. 5 shows an embodiment of the invention specifically adapted to treating the pad of a patient's finger, wherein the active and passive electrodes and the generator are integral with the primary dressing. The primary dressing, which is covered with the active electrode 1, is arranged in contact with the pad of the finger to be treated. The passive electrode 2 is arranged in contact with the outer face of the finger, without being in contact with the primary dressing. The generator 3 is arranged in the same region as the passive electrode 2. The primary dressing, the electrodes and the generator are made integral with each other by a secondary dressing 4 having the shape of a finger stall, to which they are attached.

To implement the treatment, the user simply slips the device onto the end of the finger and turns on the DC generator so as to cause treprostinil to diffuse. The direct electric current can be applied at all times the device is worn.

Once the treatment is concluded (i.e., typically after 20 minutes to 2 hours), if the device is not used as a dressing, or when the dressing is changed, if the device acts as a primary and/or secondary dressing (every 2 days, for example), it suffices to remove the device from the finger and to discard it.

Figure 6:
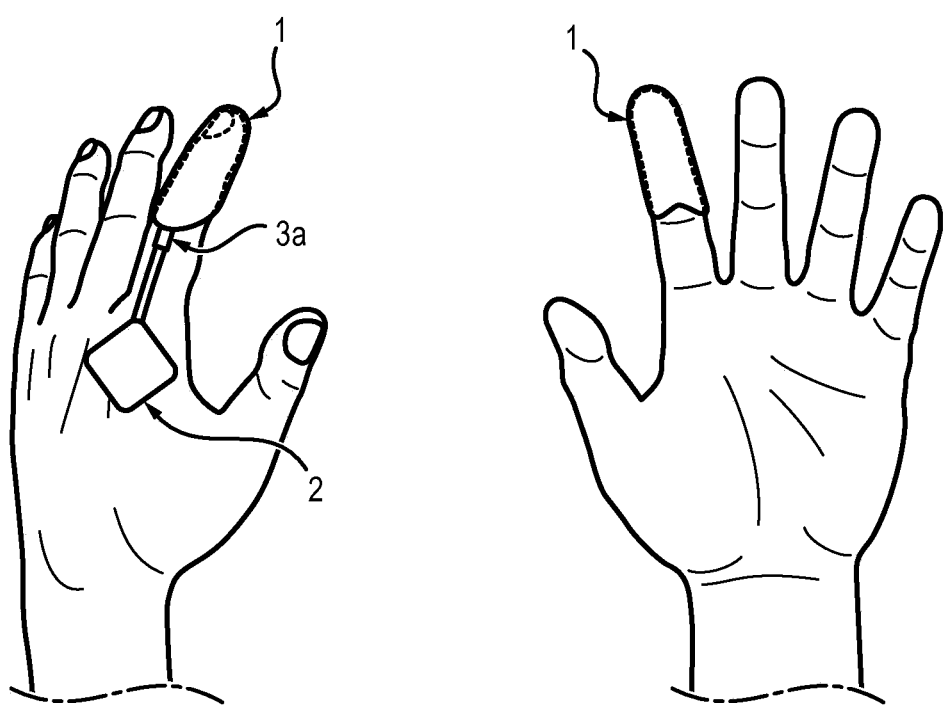
FIG. 6 is a diagram of a device according to an embodiment of the invention intended to be applied to the finger pad, wherein the passive electrode and the generator are dissociated from the primary dressing.

FIG. 6 is a diagram of a device according to an embodiment of the invention intended to be applied on the finger pad, wherein the passive electrode and the generator are dissociated from the primary dressing. In this case, the primary dressing and the active electrode 1 are provided in the form of a finger stall intended to be slipped onto the end of the finger, and being able to cover the entire circumference of the finger. As for the passive electrode 2 and the DC generator (not diagrammed here), they are attached to another region of the hand—for example, in this figure, on the back of the hand, at a distance from the finger stall.

A connector 3a makes it possible to connect the active electrode 1 to the DC generator. As in the preceding embodiment, the direct electric current can be applied throughout the time the device is worn. Once the treatment is over, it suffices to remove the primary dressing and the active electrode from the finger and to discard them. If need be, the passive electrode and the DC generator can be kept for a subsequent treatment.

Figure 7:
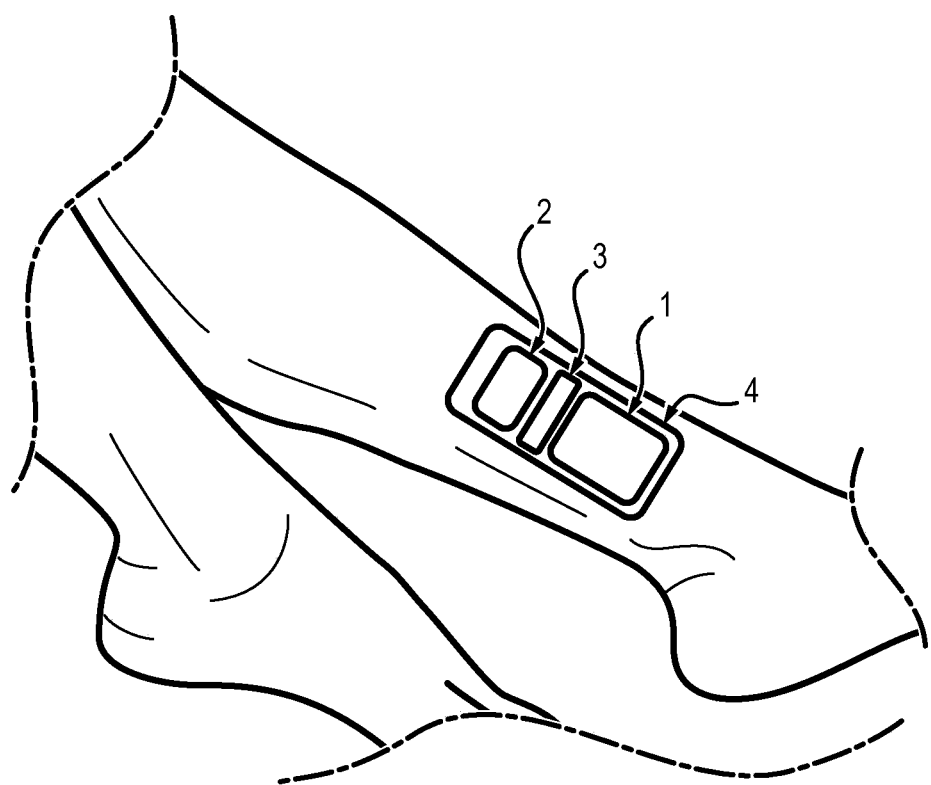
FIG. 7 is a diagram of a device according to an embodiment of the invention intended to be applied to a lower extremity of the patient.

FIG. 7 is a diagram of a device according to an embodiment of the invention intended to be applied on a lower extremity of the patient. This device can in particular be used to treat and/or prevent wounds in diabetes. As can be seen in this figure, the treated region is substantially flat, which permits the use of a substantially flat primary dressing. The surface area of said dressing can also be greater than in the case of the finger pad treatment.

In this embodiment, the treatment device integrates at the same time the primary dressing and the active electrode 1, the passive electrode 2 and the DC generator 3, which is arranged between the electrodes 1 and 2. The fastening of these various elements is provided by an adhesive support 4 that further performs the function of secondary dressing. Concerning the therapeutic indications for the device described above, scleroderma is particularly targeted. However, this application is not limiting and the device could also be used to treat and/or prevent other types of skin damage, such as macro- or microvascular ulcers of the leg, such as wounds in diabetes, for example. Furthermore, the device can be applied on any region of the patient's body according to the pathology to be treated; if the fingers (in the case of scleroderma) or the lower extremities (in the case of wounds in diabetes) are particularly concerned, the application of the device is not limited to these regions.

REFERENCES

[1] Gabrielli A, Avvedimento E V, Krieg T. Scleroderma. The New England journal of medicine. 2009; 360:1989-2003.
[2] Trojanowska M. Cellular and molecular aspects of vascular dysfunction in systemic sclerosis. Nat Rev Rheumatol. 2010; 6:453-460.
[3] Blaise S, Roustit M, Millet C, Ribuot C, Boutonnat J, Cracowski J L. Cathodal iontophoresis of treprostinil and iloprost induces a sustained increase in cutaneous flux in rats. British journal of pharmacology. 2011; 162:557-565.
[4] Blaise S, Roustit M, Hellmann M, Millet C, Cracowski J L. Cathodal iontophoresis of treprostinil induces a sustained increase in cutaneous blood flux in healthy volunteers. J Clin Pharmacol. 2012.

The invention claimed is:

1. A device for treating a digit of a human patient having a cutaneous ulcer, comprising:
a hydrogel, hydrocolloid, hydrocellular or hydrofiber primary dressing, impregnated with a volume of a treprostinil solution, that can be shaped to the contours of the digit, the primary dressing having an outer surface and an inner surface, wherein the inner surface can be applied directly on a pad of the digit, and wherein the volume of the treprostinil solution is adapted to saturate the whole primary dressing so that treprostinil molecules are in contact with the pad of the digit;
a first electrode in contact with the outer surface of the primary dressing;
a second electrode, at a distance from the first electrode, wherein the first electrode is configured to be proximate the pad and the second electrode is configured to be disposed on an outer face of the digit opposite the pad, and wherein the first electrode and the second electrode have equal surface areas; and
a DC generator having terminals that are connected to the first and second electrodes, the first electrode and the second electrode respectively forming an active electrode and a passive electrode for iontophoresis, so as to cause treprostinil to migrate by cathodal iontophoresis into the digit,
wherein the concentration of the treprostinil solution is between 0.25 mM and 25 mM.

2. The device according to claim 1, wherein the passive electrode is spaced away from and not in contact with the primary dressing impregnated with the treprostinil solution.

3. The device according to claim 1, wherein the DC generator is adapted to generate direct current having a strength between 20 µA/cm² and 100 µA/cm².

4. The device according to claim 1, wherein the DC generator is borne by a support adapted to be attached to the patient's skin.

5. The device according to claim 1, wherein:
the DC generator is integral with the primary dressing and the active and passive electrodes; and
the DC generator is a battery located between the active and electrodes.

6. The device according to claim 1, further comprising a secondary dressing that is adapted to be shaped to the contours of the digit, the secondary dressing supporting the primary dressing in contact with the first electrode, the second electrode and the DC generator.

7. The device according to claim 1, further comprising a module comprising the second electrode and the DC generator, the module being distinct from the primary dressing and adapted to be connected to the first electrode.

8. The device according to claim 1, wherein the surface area of the primary dressing is between 5 cm² and 100 cm².

9. The device according to claim 1, which is in a form adapted to be slipped onto the patient's digit, the primary dressing and the first electrode being adapted to be shaped to the pad of the digit and the second electrode is adapted to be shaped to an outer face of the digit opposite the pad.

10. The device according to claim 1, further comprising a secondary dressing that is adapted to be shaped to the contours of the digit, intended to cover the primary dressing and at least a tip of the digit.

11. The device according to claim 1, further comprising:
a connector configured to electrically connect a module, including the DC generator and the second electrode, to the first electrode;

wherein the connector is the only portion of the device configured to attach the module to the first electrode; and wherein the primary dressing and the first electrode are disposable while the module is reusable.

12. A device for treating a region of a finger of a human patient having a cutaneous ulcer, comprising:

a hydrogel, hydrocolloid, hydrocellular or hydrofiber primary dressing, impregnated with a volume of a treprostinil solution, configured to be shaped to a pad of the finger and applied directly on the pad, wherein the volume of the treprostinil solution is adapted to saturate the whole primary dressing so that treprostinil molecules are in contact with the pad;

a secondary dressing having a shape adapted to be slipped onto the finger to cover at least the tip of the finger;

a first electrode, in contact with the primary dressing;

a second electrode, configured to be shaped to an outer face of the finger opposite of the pad; and a DC generator having terminals that are connected to the first and second electrodes, the first electrode and the second electrode respectively forming an active electrode and a passive electrode for iontophoresis, so as to cause treprostinil to migrate by cathodal iontophoresis into the pad;

wherein the primary dressing, the first electrode, the second electrode, and the DC generator are fixed to the secondary dressing; and wherein the passive electrode is spaced away from and not in contact with the primary dressing impregnated with the treprostinil solution.

13. The device according to claim 12, wherein:

the second electrode is configured to be in contact with the patient's skin on the outer face of the finger; and the first electrode is on an outer surface of the primary dressing opposite an inner surface which is configured to contact a pad of the finger.

14. The device according to claim 12, wherein:

the concentration of the treprostinil solution is between 0.25 mM and 25 mM.

15. The device according to claim 14, wherein the first electrode and the second electrode have equal surface areas.

16. A device for treating a region of a finger of a human patient having a cutaneous ulcer, comprising:

a hydrogel, hydrocolloid, hydrocellular or hydrofiber primary dressing, impregnated with a treprostinil solution, the primary dressing having the shape of a finger stall configured to be slipped onto the finger and to cover the entire circumference of the finger and applied directly on the region to be treated, wherein the volume of the treprostinil solution is adapted to saturate the whole primary dressing so that treprostinil molecules are in contact with the region to be treated;

a first electrode in contact with the primary dressing;

a second electrode configured to be attached to another region of the patient's body at a distance from the primary dressing and the first electrode, wherein the first electrode and the second electrode have equal surface areas;

a DC generator arranged in the same region as the second electrode and configured to be connected to the first and second electrodes, the first and second electrodes respectively forming an active electrode and a passive electrode for iontophoresis, so as to cause treprostinil to migrate by cathodal iontophoresis through a pad of the finger and into the region to be treated; and a connector configured to connect the first electrode to the DC generator;

wherein the primary dressing and the first electrode are disposable while the second electrode and the DC generator are reusable.

17. The device according to claim 16, wherein:

the second electrode is configured to be attached to a back surface of the patient's hand that includes the finger; and the first electrode is on an outer surface of the primary dressing opposite an inner surface which is configured to contact a pad of the finger.

18. The device according to claim 16, wherein the connector is the only portion of the device configured to attach the first electrode to the DC generator.

19. The device according to claim 16 wherein:

the DC generator and the second electrode form a module; and the connector removeably connects the module to the first electrode.

20. The device according to claim 19, wherein the connector is the only portion of the device configured to attach the module to the first electrode.

21. The device according to claim 16, wherein:

the concentration of the treprostinil solution is between 0.25 mM and 25 mM; and the passive electrode is spaced away from and not in contact with the primary dressing impregnated with the treprostinil solution.

* * * * *